United States Patent
Lund Bø et al.

(10) Patent No.: US 7,293,471 B2
(45) Date of Patent: Nov. 13, 2007

(54) FLOW METER FOR MEASURING FLUID MIXTURES

(75) Inventors: Øystein Lund Bø, Randaberg (NO);
Ebbe Gustaf Nyfors, Sandnes (NO);
Rune Sørhus, Hafrsfjord (NO)

(73) Assignee: Roxar Flow Measurement AS, Stavanger (NO)

(*) Notice: Subject to any disclaimer, the term of this patent is extended or adjusted under 35 U.S.C. 154(b) by 240 days.

(21) Appl. No.: 11/063,995

(22) Filed: Feb. 24, 2005

(65) Prior Publication Data

US 2005/0188771 A1 Sep. 1, 2005

(30) Foreign Application Priority Data

Feb. 27, 2004 (NO) ................................. 20040886

(51) Int. Cl.
G01F 1/37 (2006.01)
G01F 1/74 (2006.01)
G01F 1/44 (2006.01)
G01F 1/46 (2006.01)

(52) U.S. Cl. .............................. 73/861.52; 73/861.04; 73/861.57; 73/861.65; 73/861.63

(58) Field of Classification Search ..................... None
See application file for complete search history.

(56) References Cited

U.S. PATENT DOCUMENTS

| | | | |
|---|---|---|---|
| 4,576,043 A | | 3/1986 | Nguyen |
| 4,638,672 A | | 1/1987 | McCall |
| 5,445,035 A | * | 8/1995 | Delajoud ................. 73/861.52 |
| 5,461,930 A | * | 10/1995 | Farchi et al. ............ 73/861.04 |
| 5,551,305 A | * | 9/1996 | Farchi et al. ............ 73/861.04 |
| 5,814,738 A | * | 9/1998 | Pinkerton et al. ........ 73/861.55 |

(Continued)

FOREIGN PATENT DOCUMENTS

EP 0 076 882 A1 4/1983

(Continued)

OTHER PUBLICATIONS

"Measurement of fluid flow by means of pressure differential devices inserted in circular cross-section conduits running full—Part 1: General principles and requirements", International standard, ISO 5167-1, 2003.

(Continued)

*Primary Examiner*—Harshad Patel
(74) *Attorney, Agent, or Firm*—Rothwell, Figg, Ernst & Manbeck, PC

(57) ABSTRACT

The present invention is directed to a flow meter that obtains the individual flow rates of gas, liquid hydrocarbons, and water in a predominantly gas-containing flowing fluid mixture. The flow meter comprises a water content meter (7) that provides a signal representing a measure of the water content of said fluid. The flow meter also comprises a double differential pressure generating (3) and measuring (4) structure, denoted a DDP-unit (2), that provides two measurement signals (6A and 6B) representing two independent values of differential pressure (DP) in said fluid (1). In addition to the above, the meter also comprises a signal processing unit (8) having inputs (9A-C) for receiving the measurement signals and the water content signal, and a calculation module (10) which calculates values representing the volumetric flow rates of said gas, liquid hydrocarbons and water in said fluid.

10 Claims, 11 Drawing Sheets

U.S. PATENT DOCUMENTS

| | | | |
|---|---|---|---|
| RE36,597 E * | 3/2000 | Agar et al. | 73/861.04 |
| 6,466,035 B1 | 10/2002 | Nyfors et al. | |
| 6,546,811 B2 * | 4/2003 | Fincke | 73/861.63 |
| 6,865,957 B1 * | 3/2005 | Hughes et al. | 73/861.52 |
| 6,874,374 B2 * | 4/2005 | Richards et al. | 73/861.53 |
| 6,915,707 B2 * | 7/2005 | Nyfors et al. | 73/861.63 |
| 6,935,189 B2 * | 8/2005 | Richards | 73/861.04 |

FOREIGN PATENT DOCUMENTS

| | | |
|---|---|---|
| EP | 0 738 880 A2 | 10/1996 |
| EP | 0 738 880 A3 | 10/1996 |
| FI | 69372 | 7/1985 |
| NO | 304333 B1 | 7/1991 |
| NO | 308922 B1 | 12/1999 |
| NO | 315584 B2 | 4/2003 |
| WO | WO 95/02165 A1 | 1/1995 |
| WO | WO 01/22041 A1 | 3/2001 |
| WO | WO 02/08702 A1 | 1/2002 |
| WO | WO 02/44664 A1 | 6/2002 |

OTHER PUBLICATIONS

D. Chisholm, "Flow of Incompressible Two-Phase Mixtures through sharp-edged Orifices", Journal of Mechanical Engineering Science, 1967, pp. 72-78, vol. 9, No. 1.

D. Chisholm, "Research Note: Two-Phase flow through sharp-edged Orifices", Journal of Mechanical Engineering Science, 1977, pp. 128-130, vol. 19, No. 3.

D. Chisholm, "Two-phase flow in pipelines and heat exchangers", Longman Inc, 1983, Chap. 11.

R. De Leeuw, "Liquid correction of Venturi meter Readings in Wet Gas Flow", North Sea Flow Measurement Workshop, 1997.

Ø. Lund Bø, E. Nyfors, T. Løland, J. P. Couput, "New compact Wet Gas Meter based on a microwave water detection technique and differential pressure flow measurement", 20th North Sea Flow Measurement Workshop, 2002.

E. Nyfors, "Cylindrical microwave resonator sensors for measuring materials under flow", Thesis, Helsinki University of Technology, Radio Lab., May 2000, Report S243, ISBN 951-22-4983-9.

E. Nyfors, A. Wee, "Measurement of Mixtures of Oil, Water, and Gas with Microwave Sensors. New Developments and Field Experience of the MFI MultiPhase, and WaterCut Meters of Roxar", Proc. Subsurface Sensing Technologies and Applications II, at SPIE's 45th Annual Meeting, San Diego, Jul.-Aug. 2000, pp. 12-21, Invited.

A. Sihvola, "Electromagnetic mixing formulas and applications", Inst. of Electrical Engineers, 1999, ISBN 0 85296 772 1, Ch. 9.

* cited by examiner

FLOW METER FOR MEASURING FLUID MIXTURES

This invention relates generally to flow measurements in a fluid flow.

In particular, this invention relates to the measurement of the composition or flow rates of the individual components of a fluid which is a mixture of oil, gas and water, that is, a 3-phase flow.

BACKGROUND OF THE INVENTION

In the oil industry there is in various situations a need to measure the composition and individual flow rates of a mixture of gaseous hydrocarbons, liquid hydrocarbons (oil or condensate) and water, flowing in a pipe. The conventional technique is to separate the fluid in a separator and to measure the flow of each of the components separately. During the last years also so-called multiphase meters have become available, which measure the composition and the flow rates without prior separation [1]. A special case of a multiphase flow is the so-called wet gas flow, which means that the fluid mixture is dominated by the gas phase containing small amounts of liquids. The liquid phase consists of water and of light liquid hydrocarbons (so-called condensate). Usually in a wet gas, the GVF (Gas Volume Fraction) is higher than about 95% $_{vol}$. When measuring in a wet gas flow application using a multiphase meter, the relative uncertainty achievable for the liquid component flow rates is too high.

This applicant has recently developed a wet gas meter that is capable of measuring the water content of a wet gas stream using microwave technology and the wet gas flow rate based on a differential pressure device [2,3]. The amount of liquid hydrocarbons (condensate) has in this first generation wet gas meter been calculated rather than measured. The calculation is based on a priori knowledge about the molecular composition of the hydrocarbon mixture (gas and condensate), using a PVT software package (computer software tool used to calculate thermodynamic properties like densities and gas/liquid ratios of fluids at given temperatures and pressures).

DESCRIPTION OF STATE OF THE ART

The flow rates of the components of a multiphase flow can be measured with a test separator or a multiphase meter. The test separator is expensive and bulky. Therefore, it is not practical to have a test separator measuring the production continuously on every well, but rather one test separator per oil field. This is especially true at offshore installations. Each well is routed through the test separator at regular intervals. When a well is routed through a test separator, the conditions for the well change, which may influence the production so that the measurement does not represent the average production correctly. A test separator is also slow because of the long settling time. The settling time is particularly long in wet gas applications because of the small liquid fractions and consequently long time required to fill up the separator.

Multiphase meters measure the composition of the flow and the flow speed separately [1]. From these the flow rates are calculated. Multiphase meters can be installed for the continuous, in-line measurement at every location, where measurements are needed. An important application is to install the meter subsea in the seabed production system, which is mainly a skid, mounted on top of a subsea well. If each well in a cluster of wells is equipped with a subsea multiphase meter, one common pipeline can be used to tie the cluster of subsea wells to a production platform, which may be located tens of kilometres from the cluster. The space available for a multiphase meter in a seabed production system is limited. A compact design is therefore an advantage.

A multiphase meter measures four quantities, i.e. the flow speed and the relative fractions of the three components (oil, water, and gas). It usually also needs the temperature, pressure, density of the oil and gas, and the water salinity as input parameters for compensational purposes, but these will be ignored in the following discussion of the main measurements. Theoretically, such a system can be characterized by a set of four equations, of which one equation is that the sum of the three components is 100%. Hence, a multiphase meter must be based on the use of at least three independent measurements. These three measurements can e.g. be a differential pressure (DP) measurement that essentially gives the flow velocity, a dielectric measurement that gives the water content and a nucleonic measurement giving the individual gas/liquid fractions. The uncertainty of the composition measurement used in the ordinary multiphase meters is generally to high for use in a wet gas application.

Different types of multiple DP based 2-phase wet gas meters have been suggested [4-7]. Such meters are based on the measurement of two or more differential pressures over various flow constrictions in a pipe section in order to deduce the gas and liquid rate individually. One of the suggested solutions [4] is e.g. based on a comparison of accelerational pressure drop (i.e. pressure drop caused by the acceleration of the flow) and the permanent dissipative pressure loss over a standard flow sensor (e.g. a Venturi). One disadvantage of this approach, which to a certain degree applies to multiple DP meters in general, is that it is very sensitive to the individual fluid properties. The lack of water fraction measurement in such units is consequently a factor that deteriorates its performance. Another method compares the measured differential pressures over a standard Venturi and a standard orifice [5]. The information contained in the two DP readings of separated Venturi and orifice meters has however often a poor degree of independence meaning that the uncertainty of this method with respect to the liquid detection will be relatively high. Still another solution [6] combines the DP measurements over flow elements that are installed downstream a separate mixing device. Since this solution requires three relatively extensive geometries (Venturi+mixing device+second flow element) installed in series in a pipe, the meter is quite space consuming.

Another approach to the wet gas metering has been used in the Roxar meter [2], utilizing a single DP measurement in combination with a microwave based dielectric measurement. This concept is capable of discriminating between hydrocarbons and water and hence to measure the individual flow rates of hydrocarbons and water. The split between the liquid hydrocarbons and gas is being calculated using a PVT software package (computer software tool used to calculate thermodynamic properties like densities and gas/liquid ratios of fluids at given temperatures and pressures) based on a given hydrocarbon composition.

An important drawback of the existing 2-phase multiple DP solutions is that none of the solutions discriminate between water and liquid hydrocarbons (condensate). In addition to the lack of a measurement of the individual flow rates of water and liquid hydrocarbons, this ignorance will also be associated with an increased uncertainty of the gas and liquid flow rates. The latter effect is caused by the fact that the 2-phase DP models depend on accurate knowledge about fluid properties, in particular the density but also e.g. viscosity and surface tensions. It is e.g., so that in most wet gas applications for the petroleum industry, there is a significant difference in the density of water and of the liquid hydrocarbons. While water has a density of size 1000 kg/m$^3$, the condensate density may be of size 550-750 kg/m$^3$. Ignorance of the water/liquid hydrocarbon fraction will hence be associated with a significant uncertainty of the liquid density (and of other liquid properties) which will in its turn be reflected as an uncertainty of the liquid and gas flow rate measurements.

A limitation of the concept using one single DP measurement in combination with a microwave based dielectric measurement [3] is that a measurement of the liquid hydrocarbon content of the wet gas is missing, and hence there is a requirement for having a-priori knowledge about the hydrocarbon composition.

It is an object of the present invention to provide a flow meter that overcomes the above-mentioned limitations.

In particular it is an object of the present invention to provide a true 3-phase wet gas metering concept that is capable of measuring the individual flow rates of gas, liquid hydrocarbons and water in a wet gas pipe flow.

The objects of the invention are obtained with a flow meter capable of measuring the individual flow rates of gas, liquid hydrocarbons and water in a predominantly gas-containing flowing fluid mixture. A water content meter provides a signal representing a measure of the water content of the fluid. A double differential pressure generating and measuring structure, denote a DDP-unit, provides two measurement signals representing two independent values of differential pressure (DP) in the fluid.

A signal processing unit having inputs capable of receiving the measurement signals and the water content signal includes a calculation module for calculating values representing the volumetric flow rates of said gas, liquid hydrocarbons and water in said fluid.

In another aspect of the invention there is provided a method of measuring the individual flow rates of gas, liquid hydrocarbons and water in a predominantly gas-containing flowing fluid mixture, capable of providing the individual flow rates of gas, liquid hydrocarbons and water in the stream. The method comprises providing a signal representing a measure of the water content of the fluid using a water content meter, providing measurement signals representing at least two independent values of differential pressure (DP) in the fluid using a double differential pressure generating and measuring (DDP) structure, and supplying the measurement signals and the water content signal to a signal processing unit having corresponding input channels capable of receiving the signals. Values are calculated representing the volumetric flow rates of said gas, liquid hydrocarbons and water in said fluid in a calculation unit of the signal processing unit.

THE INVENTION

The invention will now be described in more detail with reference to the appended drawings in which.

DETAILED DESCRIPTION OF THE INVENTION

Figure 1:
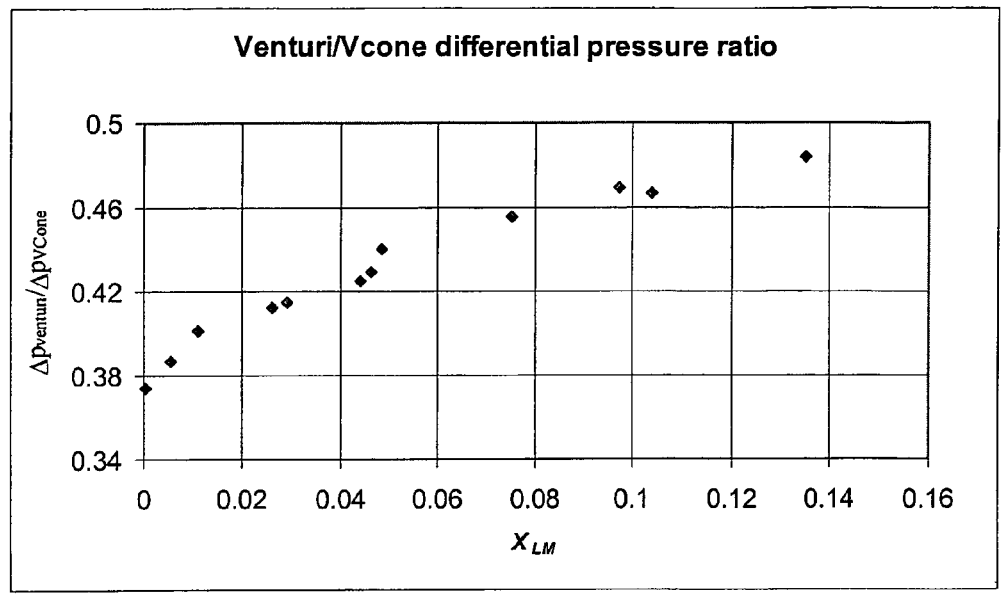
FIG. 1 illustrates an example of the measured venturi/V-Cone DP ratio as function of Lochard-Martinelli parameter for gas/water flow as measured by Roxar.

The invention is a measuring unit or meter for measuring the individual flow rates of gas, liquid hydrocarbons and water in a predominantly gas-containing flowing fluid mixture that utilizes the combination of two differential pressure measurements in combination with a water content meter 7 (e.g. using a microwave resonator) to measure the individual flow rates of gas, liquid hydrocarbons (oil or condensate) and water in a fluid pipe flow (often denoted wet gas stream) with high resolution.

The gas content can be in the range 90-100 volume-percentage, but will typically be about 95% (volume).

The water content meter 7 provides a signal representing a measure of the water content, in other words the water fraction, of said fluid flow. Two differential pressure measurements are provided by arranging a double differential pressure generating 3 and measuring 4 structures, denoted a DDP-unit 2, for obtaining two independent values of differential pressure (DP) in said flowing fluid 1. A signal processing unit 8 is arranged to receive said measurement signals and said water content signal using input units 9A-C. Input units 9A-C are typically part of the signal processing unit 8. A calculation module is associated with or coupled to said signal processing unit 8 and is adapted to calculate values representing the volumetric flow rates of said gas, liquid hydrocarbons and water in said fluid flow or fluid stream 1.

The signal processing unit 8 will typically either be located at or near a pipe section part or arranged at a remote location, e.g. together with other instrumentation. However, the invention is intended to encompass all solutions where the signal processing unit is arranged at a location which would be considered suitable by those skilled in the art.

The raw data, i.e. the digital or analogue signal representing the measurement signals could be stored in a suitable storage medium, such as a tape recorder, a CD-ROM, DVD-disc, or any other storage medium or electronic, magnetic or optical storage unit commonly known by those skilled in the art, in order that the signal processing is performed at a point in time after the time of recording the measurement signals.

This means that the signal processing could either be performed locally or non-locally, and either in real-time or at any other suitable later time.

In order to provide a better understanding of the theoretical foundations for the invention, a somewhat theoretical introduction is included in the following, in order to enable a person skilled in the art to understand the principles behind the invention.

Any non-uniform section of a pipe will result in a change of the flow speed. Based on the theory of fluid dynamics, the inertia forces required to accelerate a fluid element through such a non-uniform section is associated with a certain differential pressure. This differential pressure is related to the pipe flow rate. Consequently, a measurement of the differential pressure caused by a non-uniform section of the pipe can be used to derive the flow rate. The most frequently used structures for DP measurements are the venturi and the orifice plate. Flow measurements with such structures have been described in the international standard ISO 5167-1 [8].

The single-phase gas rate is generally given by the following standard formula [8], which applies for all the pipe flow accelerational differential pressure devices (e.g. venturi, orifice, V-Cone):

$$Q_{g0} = \frac{\pi D^2}{4} C_d \cdot y \sqrt{\frac{2 \cdot \Delta P}{\rho_g \cdot (\beta^{-4} - 1)}}, \quad (1)$$

where $Q_{g0}$ is the single phase gas flow rate [m³/s], D is the pipe inner diameter [m], ΔP is the differential pressure across the flow constriction [Pa], $\rho_g$ is the gas density [kg/m³], $$\beta = \sqrt{\frac{A_{constriction}}{A_{pipe}}} \quad (2)$$

is the beta ratio representing the relative flow cross section reduction, γ is the gas expansibility and $C_d$ is the so-called discharge coefficient representing a correction related to the fact that the effective flow constriction may differ from the physical cross section reduction.

When using DP measurements to find the mass flow in 2-phase wet gas flow, the standard formulas should be corrected for the appearance of liquid in the gas. This is usually done by the introduction of so-called two-phase multipliers that are functions of the individual fractions of gas and liquid and of the density of each of the components. The 2-phase multiplier represents the so-called overreading of differential pressure. The term overreading is used because the differential pressure with liquid present in the gas is higher than it would have been if the gas were flowing alone. The differential pressure overreading is caused by the work performed by the gas in order to accelerate the liquid phase through the flow constriction. The 2-phase multiplier, $\Phi_g$ [9-12] is defined as:

$$\Phi_g \equiv \sqrt{\frac{\Delta p}{\Delta p_g}} \quad (3)$$

where Δp is the actual differential pressure while $\Delta p_g$ is the differential pressure one would have if the gas where flowing alone. According to the Lochard-Martinelli theory, the gas rate can be written [9-12]:

$$Q_g = \frac{Q_{g0}}{\Phi_g} \quad (4)$$

where $Q_g$ is the gas flow rate in a 2-phase wet gas flow situation, $Q_{g0}$ is the gas flow rate one would get from the measured differential pressure assuming the gas flow alone according to (1), while $\Phi_g$ is the so-called 2-phase multiplier correcting for the appearance of liquids in the gas.

The 2-phase multiplier is a function of the individual fractions of gas and liquid and on the density ratio. It is usually written as a function of the Lochard-Martinelli parameter, $X_{LM}$ as:

$$\Phi_g = \Phi_g\left(\alpha_g, \frac{\rho_g}{\rho_l}\right) = \Phi_g(X_{LM}) \text{ where} \quad (5)$$

$$X_{LM} \equiv \frac{1-\alpha_g}{\alpha_g} \sqrt{\frac{\rho_g}{\rho_l}}, \quad (6)$$

$\alpha_g$ is the gas mass flow fraction, $\rho_g$ is the gas density and $\rho_l$ is the liquid density. The function (5) is an empirical correlation function, which can e.g. for a typical device be written in the form: [10-11]:

$$\Phi_g(X_{LM}) = \sqrt{1 + CX_{LM} + X_{LM}^2} \qquad (7)$$

$$C \equiv \left(\frac{\rho_g}{\rho_l}\right)^n + \left(\frac{\rho_l}{\rho_g}\right)^n \qquad (8)$$

where n is a device characteristic exponent of the order 0.1-0.5.

Once the gas rate has been found according to (4), the liquid flow rate, $Q_l$, can be calculated as:

$$Q_l = Q_g \frac{1 - \alpha_g}{\alpha_g} \qquad (9)$$

To be able to measure the individual gas and liquid flow rates in a wet gas stream using the framework in the above sections, the individual densities of the gas and liquid ($\rho_g$ and $\rho_l$) as well as the individual fractions of gas ($\alpha_g$) and liquid ($\alpha_l=1-\alpha_g$) must be known in advance. The densities can usually be found from pressure and temperature measurements combined with PVT calculations, and for the best accuracy also from an additional measurement of the water fraction, while the individual fractions of gas and liquid may often be unknown and varying.

One building block of the present invention combines two DP measurements, which contain independent information (different $\Phi_g$ functions), to determine the gas/liquid fractions. As a result, a measure of $\alpha_g$, $\alpha_l$ as well as the individual flow rates of gas and liquid can be obtained.

In constructing a double DP device for individual measurement of gas and liquid, it is an essential design criterion that the two DP readings are different in that they contain independent information. The core of constructing a double DP device for the detection of liquid content is that the two differential pressures will react differently to the presence of liquids in the gas.

In general, one could, from Eq. (1) and Eq. (4) write the measured differential pressure in the two differential pressure devices as functions of the gas fraction and of the gas flow rate:

$$\Delta p_1 = \Delta p_1(Q_g, \alpha_g) = C_1 Q_g^2 \Phi_{g1}^2 \rho_g \qquad (10)$$

$$\Delta p_2 = \Delta p_2(Q_g, \alpha_g) = C_2 Q_g^2 \Phi_{g2}^2 \rho_g \qquad (11)$$

where in the simplest model, $C_1$ and $C_2$ are constants characterizing each differential pressure while $\Phi_{g1}$ and $\Phi_{g2}$ are respectively the two-phase multipliers of the two differential pressures. According to the framework in the sections above, the differential pressure ratio goes as:

$$\frac{\Delta p_1}{\Delta p_2} \propto \left(\frac{\Phi_{g1}}{\Phi_{g2}}\right)^2 \qquad (12)$$

If the two flow meters have a difference in their response with respect to the presence of liquids in the gas, their respective two-phase multipliers will contain independent information, meaning that the differential pressure ratio will be a function (F) of the Lochard-Martinelli number and of the gas fraction and of the individual densities:

$$\frac{\Delta p_2}{\Delta p_1} = F(X_{LM}) \qquad (13)$$

$$X_{LM} = X_{LM}(\alpha_g, \rho_l, \rho_g) \qquad (14)$$

When the phase densities are known in advance, the measured differential pressure ratio can hence be used to determine the gas fraction, solving Eqs. (13) and (14) for the gas mass fraction. The liquid fraction is found from the gas fraction, because their sum must be equal to one:

$$\alpha_g + \alpha_l = 1 \qquad (15)$$

The function $F(X_{LM})$ is an empirical relation that must be defined for each flow meter device through experimental test. FIG. 1 illustrates one example of such a relation obtained by experiments carried out by this applicant on one of the example embodiments of this invention, in particular, in a gas/water wet gas flow in a venturi/V-Cone combination.

An important factor in the design of a double DP gas/liquid meter according to this invention is that the two differential pressure variables should contain independent information, which is the case in the experimental series illustrated in FIG. 1. If this is not the case, the differential pressure ratio will be a constant only and cannot be used to extract $\alpha_g$. Three main types of means which will obtain the intended results are suggested below as examples of how the present invention can be realized:

- Measuring the differential pressures over two topologically different (geometries that cannot be transformed into each other by continuous deformations) flow devices mounted immediately in series in a pipe section.
- Measuring two accelerational differential pressures at different locations of the same flow constriction.
- Measuring the accelerational differential pressure and the differential pressure related to pressure recovery of the same DP device.

One type of double DP realization (DDP-unit) can be constructed by the use of two topologically different differential pressure (DP) generating structures 20, 21A-C, for example two flow constrictions installed close to each other, for example mounted in series in a pipe section, such that one DP-generating structure disturbs the flow pattern at the other DP-generating structure. This solution utilizes the fact that the DP overreading depends significantly on the flow pattern, i.e. how the liquid phase is distributed in the gas. The overreading is e.g. different if the liquid flows as a thin film at the inner wall of the pipe (annular flow) compared to a case where it flows as droplets immersed in the gas phase (mist flow).

One DP-device can be made by a narrowing of the pipe diameter, while the other DP-device is constructed by the insertion of a body on the pipe. This difference in topology makes a difference in the flow pattern downstream the devices. One DP-device will in this case create a flow pattern immediately downstream the device with radially outward pointing velocity components, while the other DP-device will create velocity components pointing radially inward. Such a difference can be utilized for creating differential pressure overreadings containing independent information that is used to extract flow rate and liquid content. The two DP devices should be installed close to each other in the pipe to maximize the difference between the two. The upstream device will then have a fully developed annular/mist pipe flow regime as its inlet conditions, while the downstream device will have a flow regime at its inlet that is being influenced by the upstream DP-device.

Figure 2:
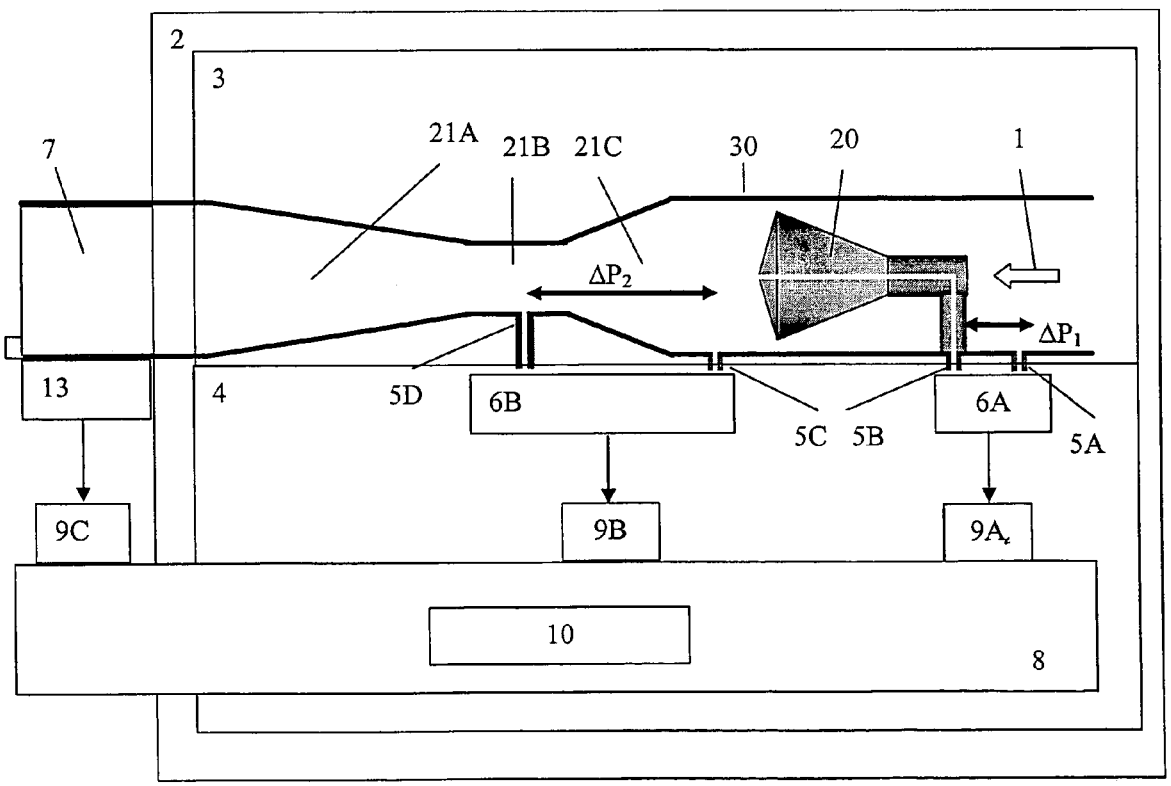
FIG. 2 illustrates a first example of a combined water content meter and DDP-unit according to the invention using a V-Cone upstream and venturi downstream.

FIG. 2 shows an example embodiment of the present invention wherein a DDP-unit 2 comprises a double differential pressure generating part 3 and a corresponding double differential pressure measuring part 4. A fluid flow 1 inside flowing inside a pipe 30 is shown, the flow having a flow direction from right to left in this example. The fluid flow 1 first encounters an upstream element, a first differential pressure generating device 20, in this case a V-cone structure 20 [10] for generating a first differential pressure $\Delta P_1$ in the fluid flow. Two pressure taps 5A, 5B are located near the V-cone structure 20. Coupled with the pressure taps 5A, 5B is a corresponding differential pressure transmitter 6A of a type well known to those skilled in the art, for transmitting differential pressure signals to corresponding signal interfaces 9A of a signal processing unit 8.

Downstream from the V-cone 20 is a second differential pressure generating device 21A-C, in this example a venturi, for generating a second differential pressure $\Delta P_2$. The second differential pressure will be independent of the first differential pressure provided the first (upstream) differential pressure generating device is placed immediately upstream of the second (downstream) differential pressure generating device. A second set of pressure taps 5C, 5D are arranged together with corresponding differential pressure transmitter 6B in order to generate and transmit a signal representing this second differential pressure to the signal processing unit 8.

At the inlet of the first differential pressure (DP) generating device, the flow is more annular-like where the liquid tends to flow as a film. Immediately downstream of the first DP element, on the other hand, there is a flow region with large turbulence, a circulating flow and vortex shedding that tends to mix the liquid into the gas core. When the downstream element (a venturi in the example) is placed immediately downstream of the first device, this situation means that the liquid is entrained more into the gas core at the inlet of the downstream flow meter, a factor that will increase the difference between the two differential pressure devices.

A water content meter 7 is arranged, for example directly coupled with the pipe 30, for generating and transmitting a signal representing the water content of the fluid flow to the signal processing unit 8 via a suitable signal interface 9C coupled to the signal processing unit 8.

The signal processing unit 8 comprises a calculation module 10 for performing the steps in the processing of the signals received from the differential pressure transmitters 9A and 9B and from the water content meter signal interface 9C.

Figure 3:
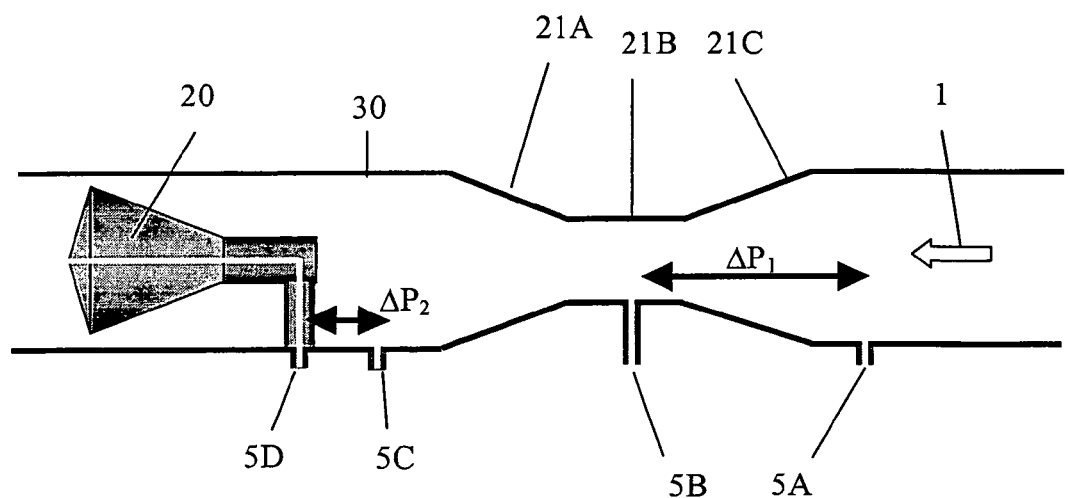
FIG. 3 shows a second example of an embodiment of a DDP-unit according to the invention using venturi upstream and V-Cone downstream.
Figure 4:
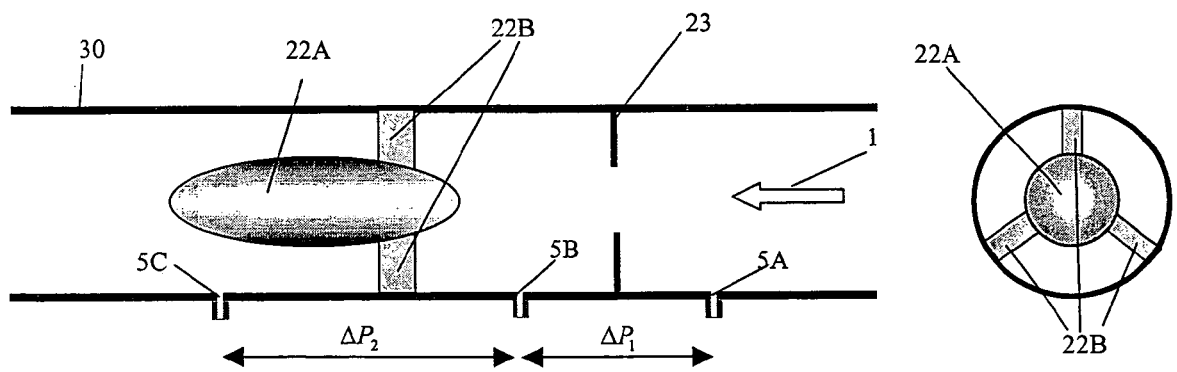
FIG. 4 shows a third example of an embodiment of a DDP-unit according to the invention using an orifice upstream and an ellipsoid shaped centred body downstream.

Another realization of the double differential pressure generating device 3 which is a part of the present invention is shown in FIG. 3. The order of the two differential pressure generating devices has been swapped compared with FIG. 2, now using a venturi 21A-C as the upstream element and a V-Cone 20 as the downstream element. Still another example is sketched in FIG. 4 using an orifice 23 as the upstream element and an ellipsoid shaped body 22A installed in the pipe centre as the downstream element.

Figure 5:
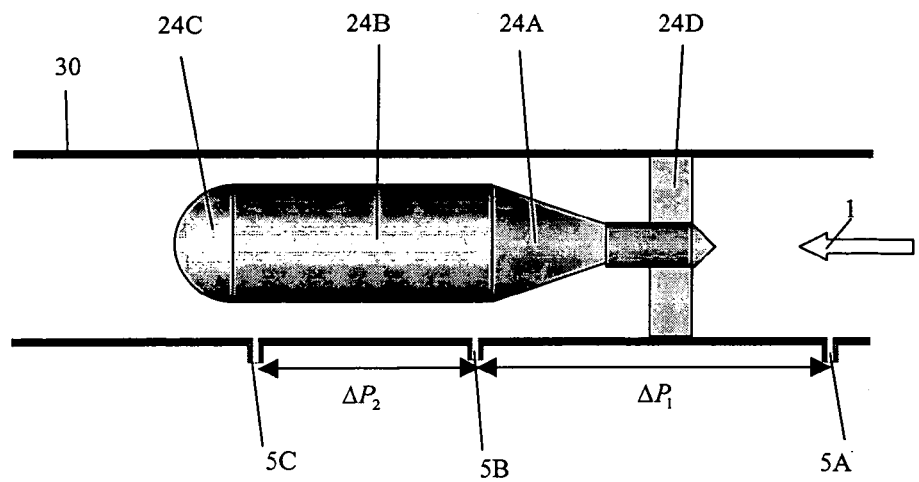
FIG. 5 illustrates a first example of a compact double accelerational differential pressure device according to the invention with a body in a pipe section.
Figure 6:
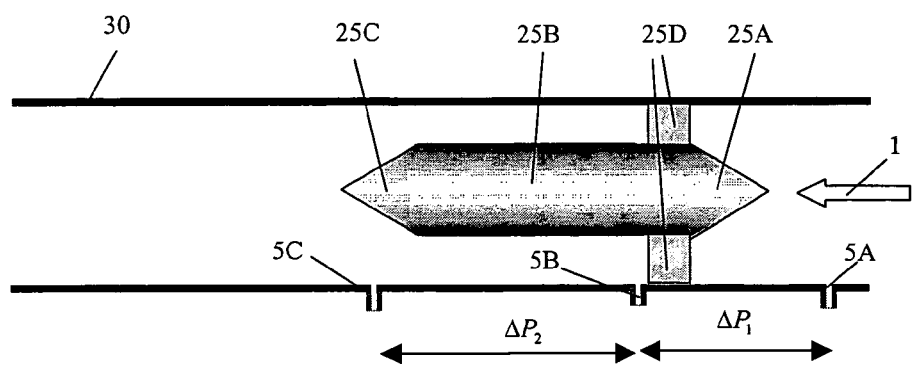
FIG. 6 shows a second example of a compact double acceleration differential pressure device according to the invention with a body in pipe section.

A compact version of a double DP device can be constructed by the measurement of two accelerational pressure drops at or near the same flow constriction. The basic physics behind such a realization is based on the difference in inertia of the two phases, due to the difference in density. The flow constriction will typically be a single flow cross section reducing device mounted in said stream 1, such as to vary the cross section of said stream Two differential pressure measuring structures are arranged to measure differential pressures at two different positions along said flow cross section reduction device. The geometry of the DP device (which can also be used as a microwave sensor element) consists of a centred oblong body 24B inserted in the centre of a pipe section 30, as illustrated in FIGS. 5 and 6. The insertion body 24B, 25B has an inlet or entrance region where the flow cross section is reduced followed by a mid region with a substantially constant reduced flow cross section, and finally by an outlet or exit region where the flow cross section again is increased to its full value. In some versions the entrance region is followed immediately by the exit region, thus there is no mid region. The idea is that the light gas phase, which is also the continuous phase in a wet gas application, will be accelerated first, in the inlet region. Drag forces from the gas will, in its turn, accelerate the liquid phase and will happen subsequently to the gas acceleration. This means that the differential pressure measured at the inlet region will be dominated by the gas acceleration, while the acceleration of the liquid phase will tend to have a larger effect on the second DP measurement in the straight section. Expressed in general terms, a DDP-unit 2 is arranged to have a first differential pressure measuring device arranged in one of the said regions, and a second differential pressure measuring device in another one of said regions. Both of these DP-measuring structures could be arranged in to measure accelerational pressures. In another version one DP-measuring structure is arranged to measure accelerational pressure and the other DP-measuring structure is arranged to measure pressure recovery. The DP so obtained ratio $\Delta P_2/\Delta P_1$ will hence contain information about the liquid content. At lower liquid contents this ratio will be low, while at higher liquid contents, the ratio will increase.

The dependence can be written in the form (10) but the exact form must be established experimentally for each new geometry.

Figure 7:
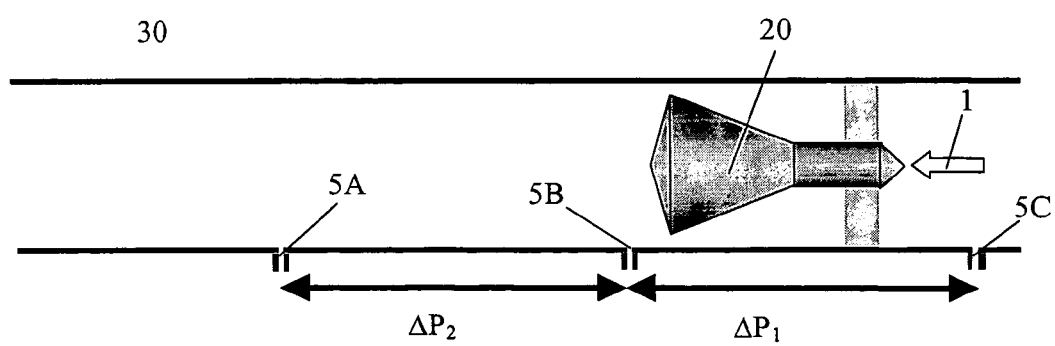
FIG. 7 shows a first example of an embodiment of the invention with a double DP—acceleration/recovery device.
Figure 20:
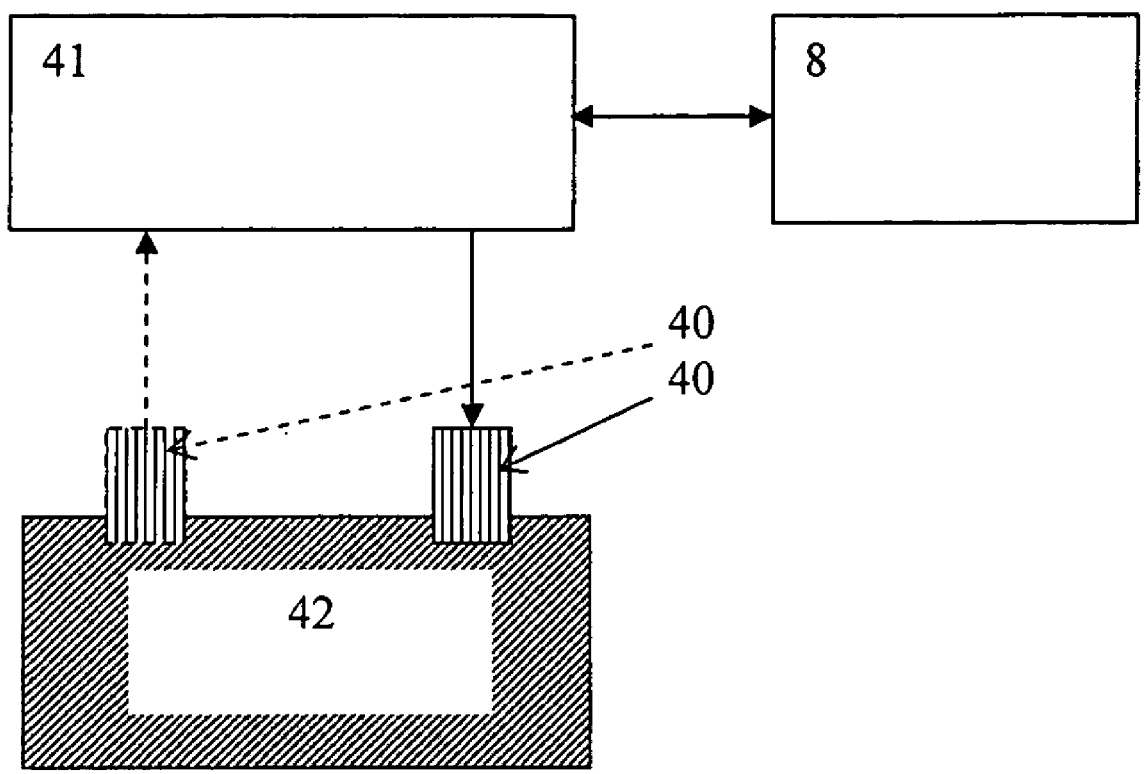
FIG. 20 shows an illustration of how a microwave sensor is connected with the microwave drive electronics and the signal processing module

Still another possible solution to the double DP measurement that can be combined with a microwave water fraction meter is to measure and compare the accelerational differential pressure and the pressure recovery over the same flow constriction. This embodiment of the invention thus constitutes an improvement as compared to the type of measurement that is utilized in the patent in Ref. [4] where a venturi meter is utilized for 2-phase gas/liquid flow. The principle of the present invention is however not limited to a venturi but can also be realized using a centred body as the DP element, in which case the flow meter may also comprise a dielectric permittivity measuring unit, for example a microwave measuring unit including a microwave resonator or sensor 40, microwave drive electronics 41 and associated microwave signal processing functions being a part of the signal processing module 8, for example the version whose geometry is illustrated in FIG. 7 and the schematic of the measurement as illustrated in FIG. 20. Details of the operation of a V-cone are explained in reference [3], Norwegian patent No. 315584, which is hereby incorporated by reference. The latter combinations will be one possible solution to a 3-phase wet gas metering concept a full 3-phase wet gas meter.

A compact version of this principle can be realized by introducing a sudden change in flow cross section (turbulence generating geometry) to an otherwise more smooth geometry and to measure two differential pressures within the reduced flow cross-section. These two differential pressures will then have a certain difference in the relative size of the acceleration and dissipation related differential pressures. Examples of such structures are shown in FIGS. 8-9.

Figure 8:
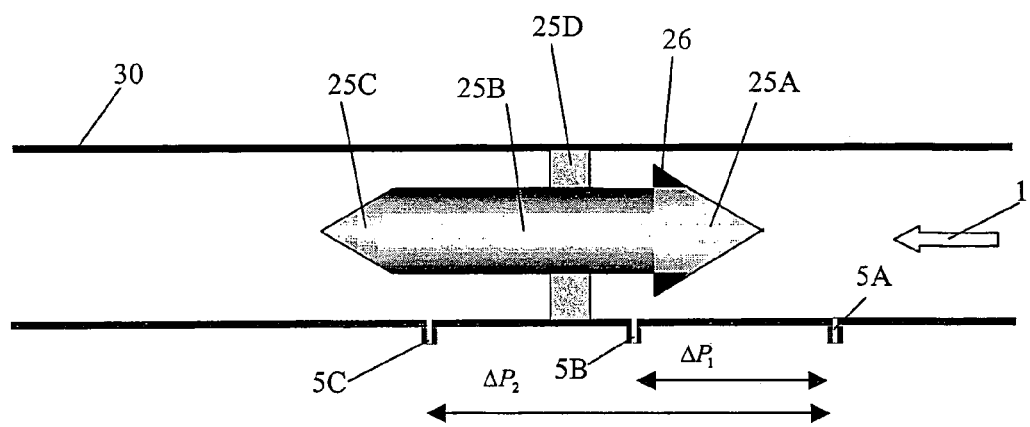
FIG. 8 shows a second example of an embodiment of the invention with a double DP—acceleration/dissipation device.

FIG. 8 illustrates a DDP-generating unit similar to the one in FIG. 6, with the addition of a turbulence generating geometry 26 at one end of the oblong body 25B inserted into the pipe section 30.

Figure 9:
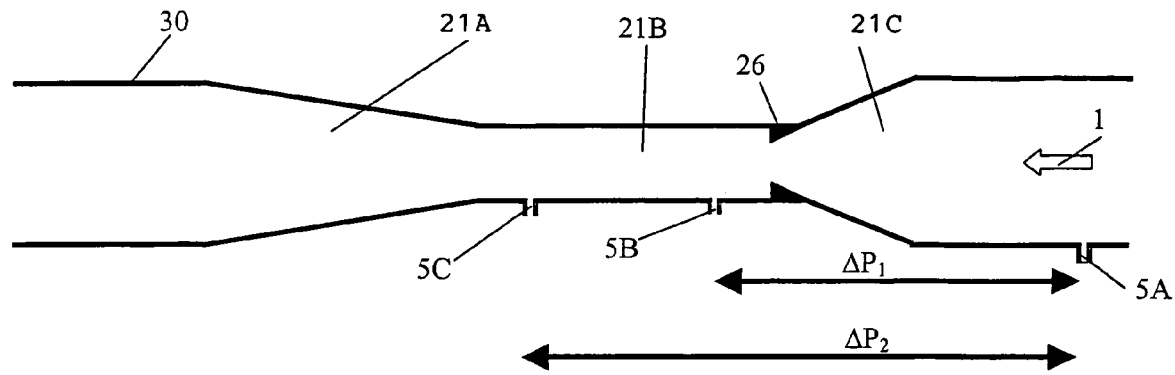
FIG. 9 shows an third example of an embodiment of the invention with a double DP—acceleration/dissipation device.

FIG. 9 illustrates an alternative embodiment of the DDP-generating structure in which a turbulence generating structure geometry 26 is arranged as a part of the venturi 21B-C, e.g. attached to the pipe walls at one end of the narrow section of the venturi. In FIGS. 8 and 9 the turbulence generating geometry 26 provides an abrupt change of the diameter of the flow section.

In the following section the basics of dielectric permittivity based composition measurements are outlined. When two material components (A and B), (liquid, gas, or solid particles), with different permittivity ($\in_A$ and $\in_B$) are mixed, the mixture has a permittivity $\in_m$ that is dependent on the mixing ratio $\alpha$ of the two components [14]. The mixing ratio is usually expressed as the total volume of one of the components relative to the volume of the mixture, e.g.

$$\alpha_A = \frac{V_A}{V_A + V_B} \quad (16)$$

where $V_A$ is the volume of component A and $V_B$ is the volume of component B in a sample of volume $V_m = V_A + V_B$ of the mixture. If e.g. A is water and B is gas, $\alpha_A$ is the water content (water volume fraction) of the mixture. In the case of the fluid produced in a wet gas well, B may be a known mixture of gas and liquid hydrocarbons, and will therefore be generally called the hydrocarbon component. The way $\in_m$ depends on $\alpha_A$ depends on how the components mix with each other and is therefore specific for these components. As a model for this dependence, a known model [14] may be used, or an empirical calibrated model. The Bruggeman formula [14] has e.g. demonstrated to be a good mixing model in the case of hydrocarbon-water mixtures.

The water fraction ($\alpha_w$) in a hydrocarbon based wet gas can e.g., by the use of the Bruggeman formula be expressed as:

$$\alpha_w = 1 - \frac{\varepsilon_w - \varepsilon_{mix}}{\varepsilon_w - \varepsilon_{hc}} \cdot \left(\frac{\varepsilon_{hc}}{\varepsilon_{mix}}\right)^{1/3} \quad (17)$$

where $\in_w \gg 1$ (typically ~80) is the water permittivity, $\in_{hc} \sim 1\text{-}2$ is the hydrocarbon permittivity, and $\in_{mix}$ is the measured mixture permittivity.

In the following the basics of microwave microwave resonators are outlined. One example of how the measurement of permittivity can be realized is by the use of a microwave resonator. Such a sensor has a resonant frequency that is dependent on the permittivity of the medium with which it is filled. If $f_0$ is the resonant frequency of the sensor, when it is empty, and $f_m$, when it is filled with the mixture, the permittivity of the mixture is [17]

$$\varepsilon_{mix} = \left(\frac{f_0}{f_{mix}}\right)^2 \quad (18)$$

The basics of microwave resonators have been described in e.g. [17].

A microwave resonator can be realized as an electromagnetic cavity between two reflecting discontinuities [17]. When a microwave resonator sensor is implemented in a pipe for the purpose of measuring the permittivity of the fluid that is flowing in the pipe, the discontinuities must have a structure that is open enough so that the fluid can pass through the sensor. One practical type of discontinuity is an increase in the cut-off frequency [17]. If the resonant waveguide has a cut-off frequency that is lower than that of the pipe, and the resonant frequency of the used mode is the same as the cut-off frequency, the energy cannot propagate in the pipe. No other reflecting discontinuity is therefore needed.

Microwaves can propagate along a large variety of structures. There is no reason why the structure should even be uniform. Therefore, the cross section of the resonant structure inside the pipe can be different at different locations along the structure. In the case of non uniform structures, the wave mode is inhomogeneous and can generally neither be described by any wave modes known from the literature nor be solved analytically. In such cases, the resonant frequencies and field distributions can be solved approximately by numerical methods using e.g. FEM (finite element method) software. Any structure with a resonant frequency that is lower than the cut-off frequency of the pipe can in principle be used as a resonator sensor [17].

Figure 10:
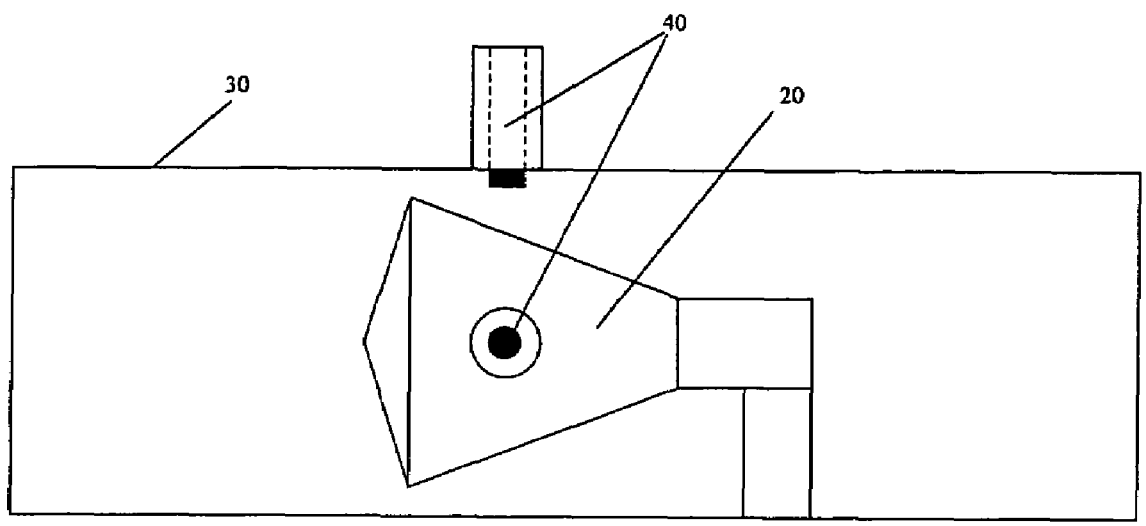
FIG. 10 illustrates a V-Cone with microwave antennas for water detection (Prior art)

Several examples (based on venturi tubes, orifices, V-Cones) of how to realize a combined geometry to be used as microwave resonator and differential pressure flow meter are described in [3]. One example is the V-Cone geometry shown in FIG. 10. This structure will behave as a microwave resonator. The electromagnetic behaviour of the V-Cone sensor can be viewed as a ¼ wavelength coaxial resonator where the electromagnetic energy is confined in the microwave cavity as defined by the V-Cone length. This structure has an advantageous electromagnetic field distribution that makes it well suited for water fraction detection in a wet gas stream:

In the axial direction, the field has its maximum at the cone edge were the gas velocity is highest. The water content will hence be measured at this location.

The field is uniformly distributed along the circumference of the gap, making the sensor less flow regime dependent.

Figure 11:
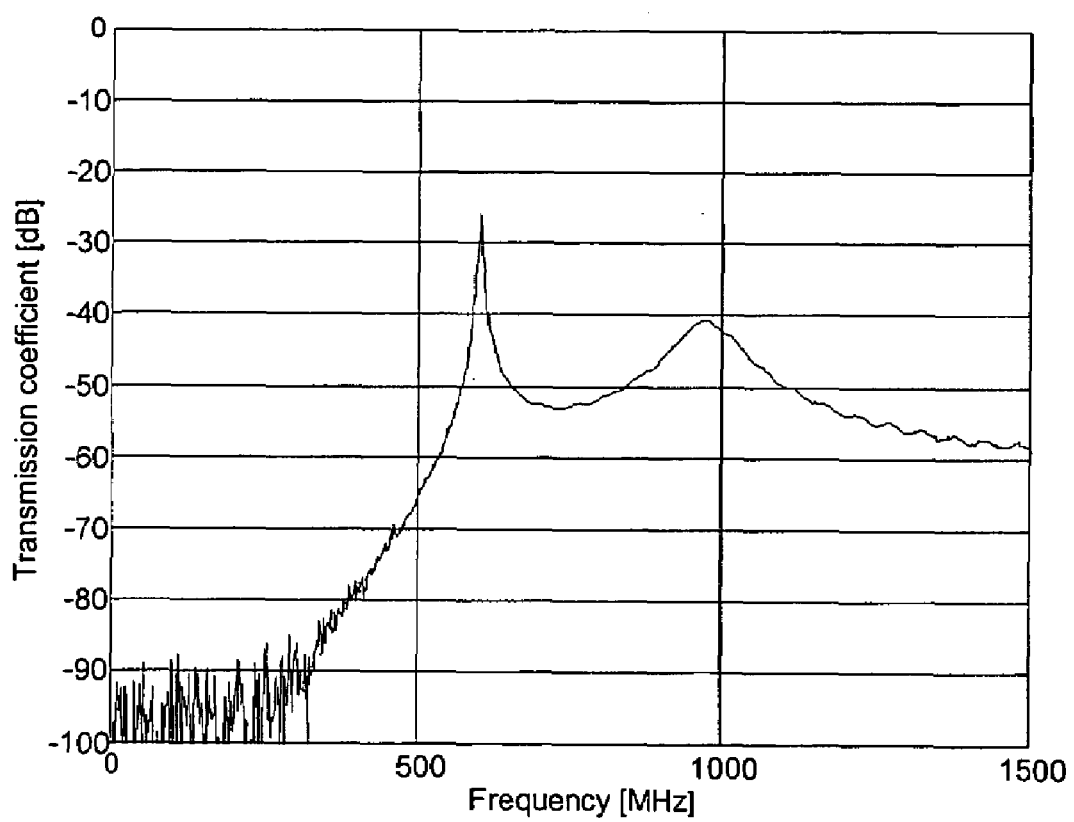
FIG. 11 shows an example of a microwave response of a V-Cone sensor.

Computer simulations of electromagnetic fields using the FEM method as well as measurements have shown a frequency response with a clean and single resonance peak in the actual frequency range, see the example curve in FIG. 11.

A 3-phase wet gas meter for the individual measurements of gas, liquid hydrocarbons and water flow can be constructed by a combination of a double DP flow metering device and a separate water fraction detection sensor. The water fraction unit may e.g. be based on any type of dielectric measurement that gives a measure of the mixture permittivity. The microwave resonator is one practical solution to the dielectric measurement that can be employed together with the double DP measurement to constitute a sensitive and compact realization of a 3-phase wet gas-metering concept.

Figure 12:
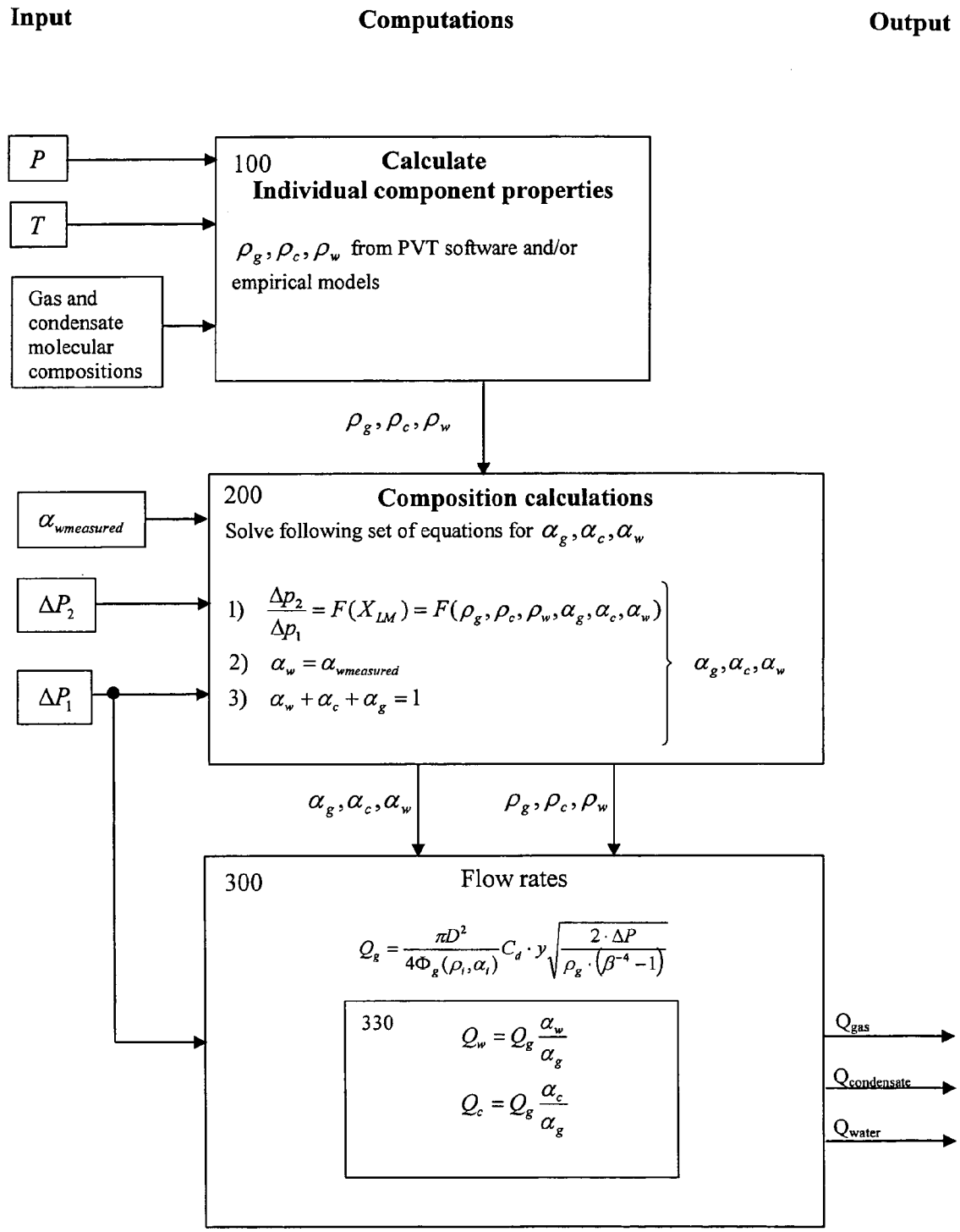
FIG. 12 is a schematic diagram illustrating the steps involved in the signal processing modules and their interaction for the 3-phase wet gas flow meter according to the present invention, based on a double DP and a water fraction measurement.
Figure 13:
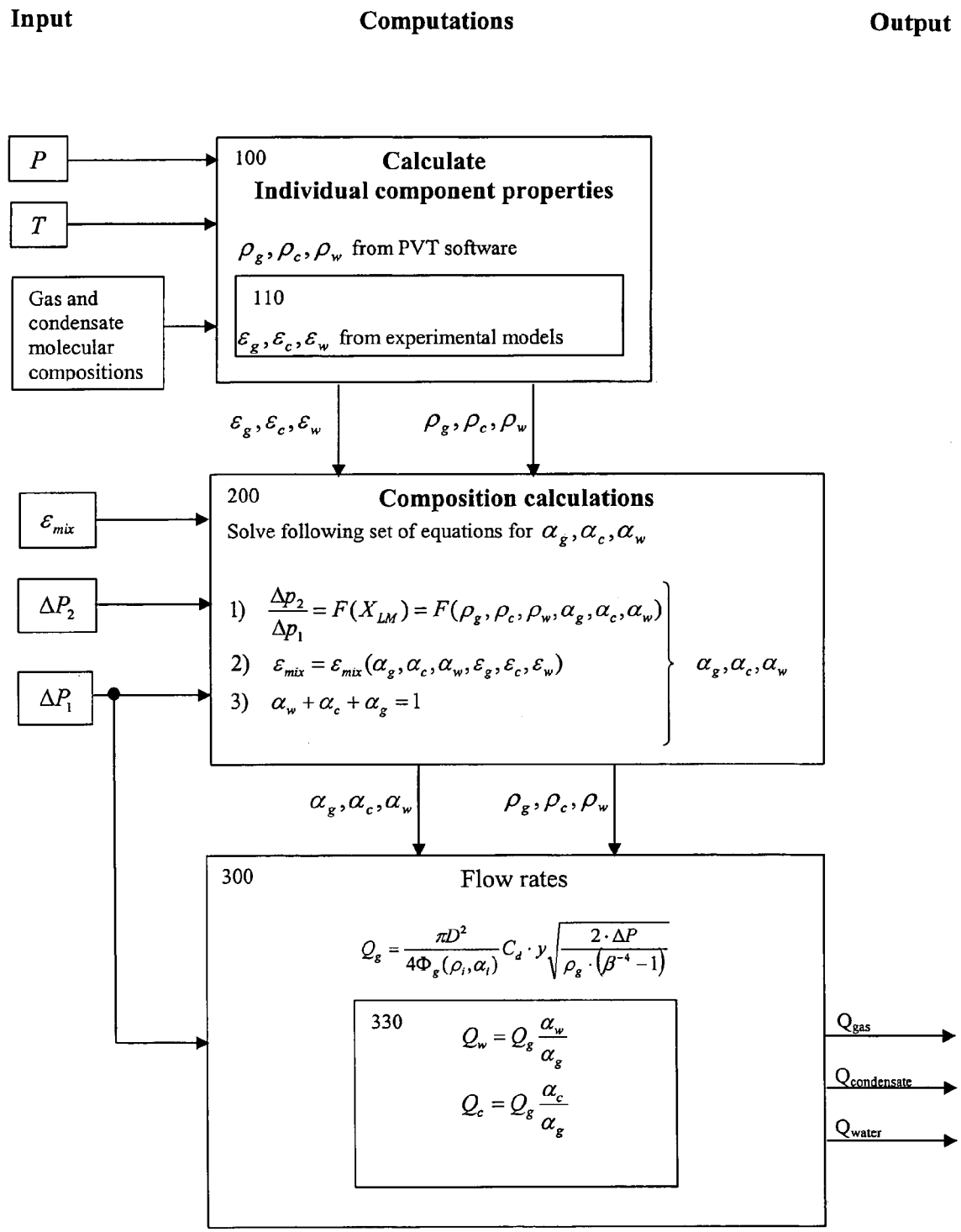
FIG. 13 is a schematic diagram illustrating the steps involved in the signal processing modules and their interaction for the 3-phase wet gas flow meter according to the present invention, based on a double DP and a dielectric water fraction measurement.

The signal processing unit 8 of the 3-phase meter according to the invention comprises modules for performing the computational steps illustrated in the flow diagram in FIG. 12 and FIG. 13. FIG. 12 shows the computational modules that can be used in the case that a general water content meter is combined with a DDP unit, while FIG. 13 shows the computational modules in the particular case that the water content meter is based on a dielectric measurement of the permittivity of the fluid mixture.

1) In module 100 and the submodule 110, the individual properties of gas, liquid hydrocarbons and water are calculated based on the measured or given temperature and pressure and on the given molecular composition of gas and liquid hydrocarbons. In module 100 the individual densities ($\rho$) of gas, liquid hydrocarbons, and water are calculated based on the measured temperature and pressure using empirical models or e.g. from a PVT software module.

$$P, T, \xrightarrow{PVT,\text{Models}} \rho_g, \rho_c, \rho_{ww}$$

In the case of a dielectric measurement of water fraction (FIG. 13), the individual gas, liquid hydrocarbons and water permittivities are calculated in block 110 from the given components individual densities, from pressure and temperature based on empirical models $$P, T, \rho_g, \rho_c, \rho_w \xrightarrow{\text{Models}} \varepsilon_g, \varepsilon_c, \varepsilon_w$$

1) In module 200 the composition of the fluid flow is calculated based on the measured differential pressure ratio and the measured water fraction. In the case of a general water fraction meter (FIG. 12), the measured water fraction is an input to the computational module. The 3 unknown ($\alpha_w, \alpha_c, \alpha_g$) are found solving the following set of equations $$\left.\begin{array}{l} 1)\ \dfrac{\Delta p_2}{\Delta p_2} = F(X_{LM}) = F(\rho_g, \rho_c, \rho_w, \alpha_g, \alpha_c, \alpha_w) \\ 2)\ \alpha_{w\,measured} = \alpha_w \\ 3)\ \alpha_w + \alpha_c + \alpha_g = 1 \end{array}\right\} \alpha_g, \alpha_c, \alpha_w$$

where $F(X_{LM})$ is an empirical calibration model. This set of equations must normally be solved numerically by iterative computer means). In the case that a dielectric water fraction detection method (e.g. a microwave sensor) is being used for water detection (FIG. 13) the measured mixture permittivity is the basis for the composition measurement and the set of equations can be written:

$$\left.\begin{array}{l} 1)\ \dfrac{\Delta p_2}{\Delta p_2} = F(X_{LM}) = F(\rho_g, \rho_c, \rho_w, \alpha_g, \alpha_c, \alpha_w) \\ 2)\ \varepsilon_{mix} = \varepsilon_{mix}(\alpha_g, \alpha_c, \alpha_w, \varepsilon_g, \varepsilon_c, \varepsilon_w) \\ 3)\ \alpha_w + \alpha_c + \alpha_g = 1 \end{array}\right\} \alpha_g, \alpha_c, \alpha_w$$

In the case that the dielectric water detection unit is a microwave resonator, the mixture permittivity is found from the measured resonant frequency based on Eq. (18). The output from the module 200 is the individual volume flow fractions of gas, liquid hydrocarbons and water.

2) In module 300 the gas flow rate is computed from one of the measured differential pressures and from the calculated fractions according to the scheme in Eq. (1)-(5):

$$\Delta p_1 \rightarrow Q_g$$

3) In module 330 the final step of computing liquid hydrocarbons and water flow rates is performed based on calculated fractions and gas rate:

$$\alpha_g, \alpha_c, \alpha_w, Q_g \rightarrow Q_c, Q_w$$

Figure 14:
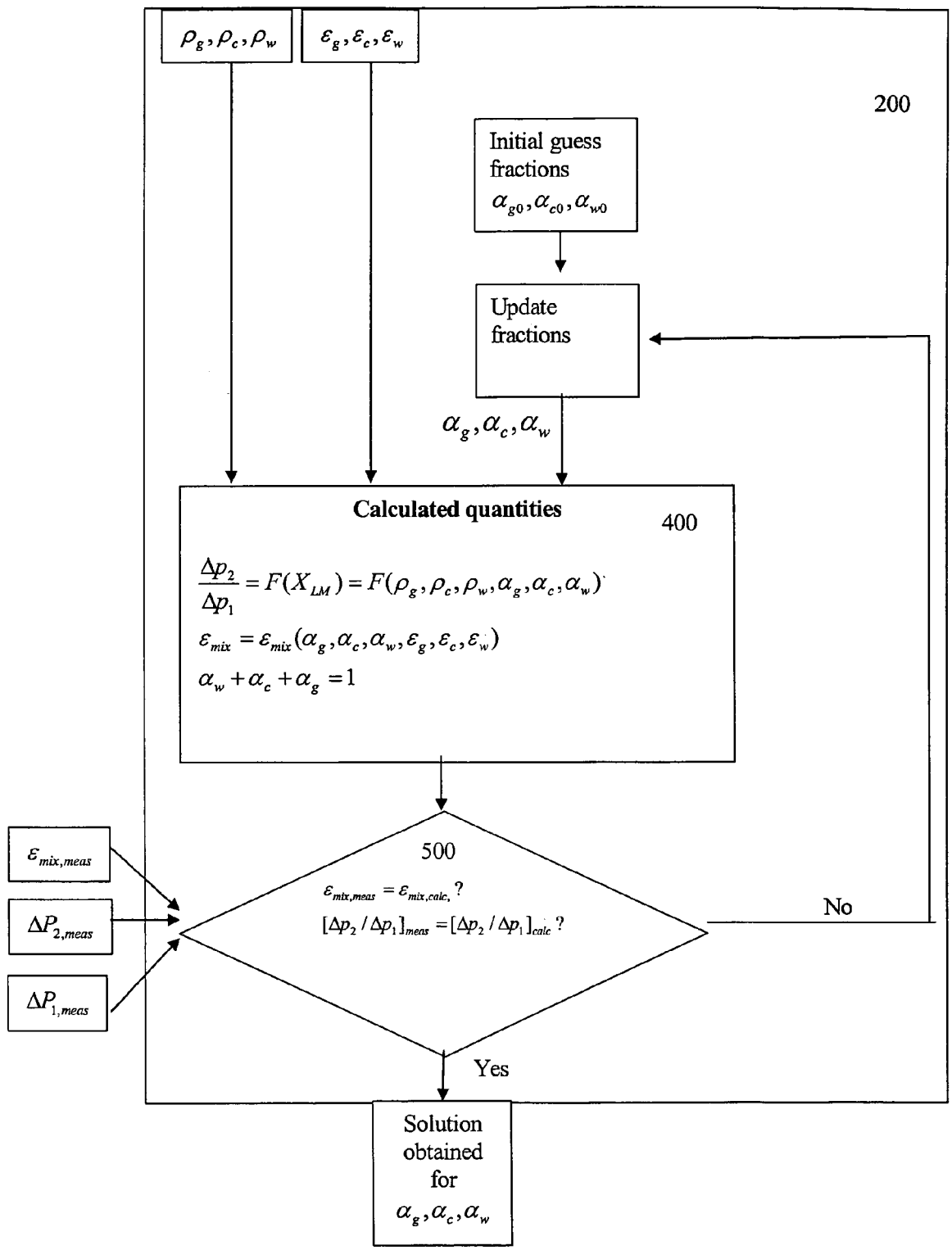
FIG. 14 is a schematic flow diagram illustrating the iterative computer steps used in the 3-phase wet gas flow meter according to the present invention for calculating fluid fractions from raw measurements and input data.
Figure 15:
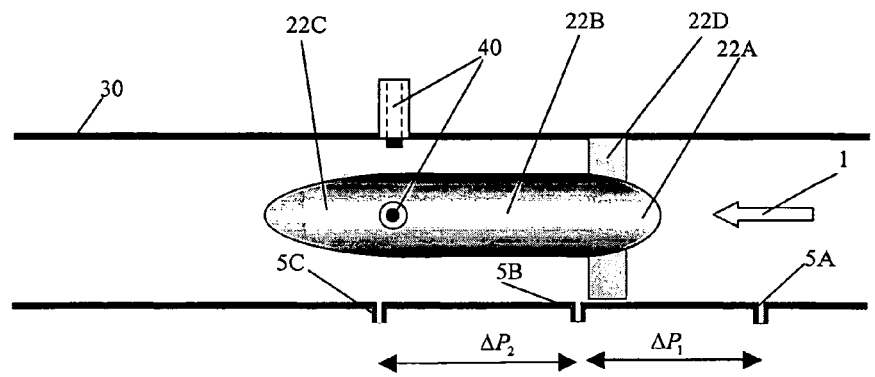
FIG. 15 shows an example of an embodiment of a 3-phase wet gas meter according to a compact version of the invention based on a combined double DP and a microwave sensor.
Figure 16:
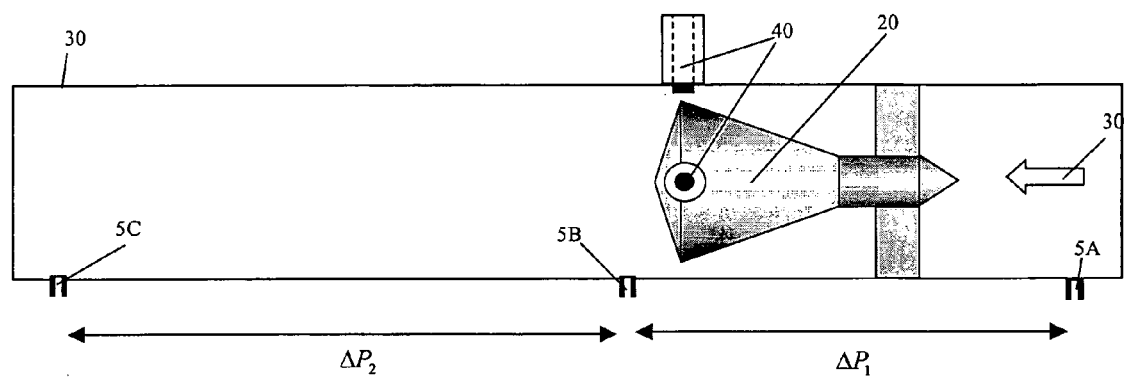
FIG. 16 shows another example of an embodiment of a 3-phase wet gas meter according to a compact version of the invention based on a V-Cone flow meter.
Figure 17:
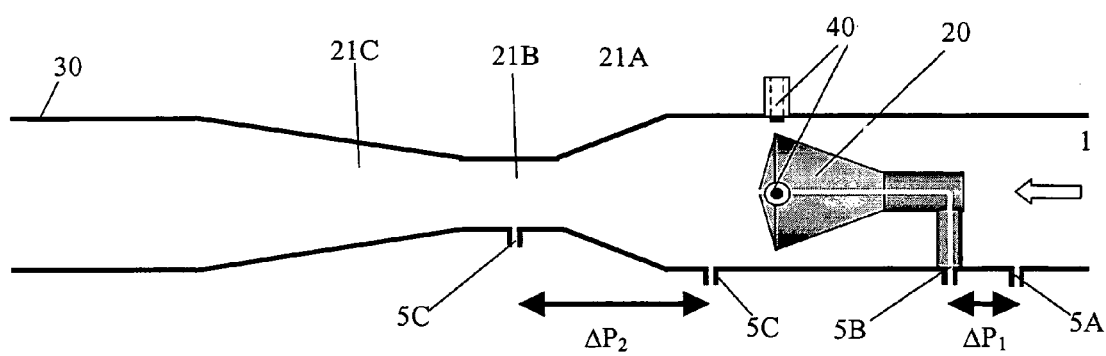
FIG. 17 shows another example of an embodiment of a 3-phase wet gas meter according to the invention.
Figure 18:
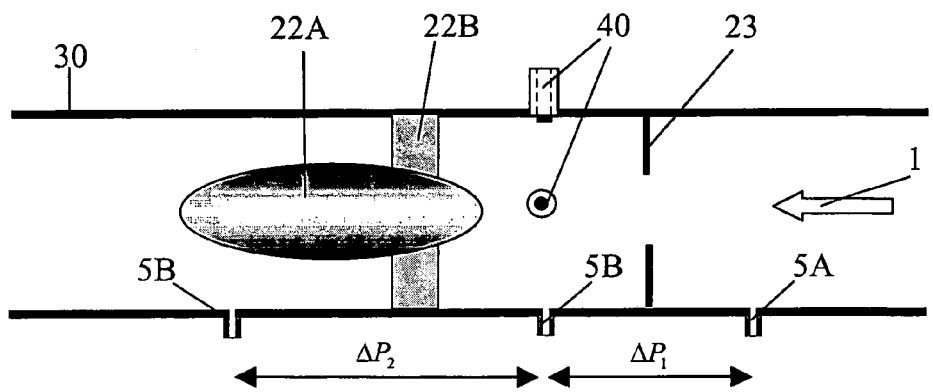
FIG. 18 shows another example of an embodiment of a 3-phase wet gas meter according to the invention.

FIG. 14 illustrates how the computation in the 3-phase wet gas flow meter according to the present invention may comprise an iteration procedure as part of the calculation of fluid fractions as in block 200 of FIG. 13 from raw measurements and input data.

An initial guess of the fractions of the fluid flow is initially supplied together with the density and dielectric permittivity of the gas, water and liquid hydrocarbons from module 100 and 110 to a calculation module performing the estimation of quantities of gas, water and liquid hydrocarbons.

Based on the supplied input signals, values are calculated 400 for the differential pressure ratio $\Delta P_2/\Delta P_1$, and the permittivity of the mixture, $\varepsilon_{mix}$. These calculated values are compared 500 with the measured values. In the case that the calculated values differ from the measured values by less than a given amount, the calculated and measured values are deemed to be equal, and the present input values for the fractions constitute the desired result.

In the case that the calculated values and the measured values differ by an amount larger than a given value, a signal is given to the update fractions module in order that a new update or a new calculation of the fractions may be computed. Typically, a computation will be performed using a Newtons method or other similar techniques known to those skilled in the art, based on the measured and estimated values.

The new calculated fractions will is then the new input to the calculation and comparison. This iteration will typically be performed a number of times until a solution is obtained, i.e. until calculated quantities are equal to the measured quantities within a given tolerance or a given error margin.

The various functions and modules of the signal processing module above will typically be realized as computer program code or software adapted to operate in a signal processing module being a part of a general-purpose computer, microprocessor, or computing device known to those skilled in the art or a custom made embedded microprocessor.

A 3-phase wet gas meter can e.g. be realized by a number of different combinations of one of the double DP devices described above in combination with one of the microwave resonators listed in Ref [3], the full content of which is hereby incorporated by reference. A few examples of possible realizations are shown in FIG. 15-18. FIGS. 15-18 illustrate examples of the arrangement of microwave coupling structures 40, which can be e.g. probes, loops, irises, or combinations of such, in order to be able to excite and measure an electromagnetic field within the resonating structure 42, see e.g. pp. 40-43 in [17]. The microwave resonance can be measured with various techniques known to anyone skilled in the art, based on e.g. the measurement of the reflection (requires one coupling device only) or transmission (requires two coupling devices) of microwaves, as described on pp. 30-37 in [17]. Any type of suitable microwave drive electronics known to anyone skilled in the art may be used as schematically illustrated in FIG. 20 to provide a suitable signal interface to the microwave coupling structures 40. Such a drive 41 unit will typically comprise an output module to provide output signals to the microwave coupling structures 40 for exciting a microwave field and a signal receiving module for receiving signal from microwave coupling structures representing a characteristic property of the microwave field within the resonating structure 42, e.g. the amplitude or phase of the microwave field typically characterized in terms of the reflection or transmission coefficient of the resonator. The drive electronics 41 may either be locked to the resonant frequency (see e.g. pp. 125-130 in [17]), or measure the reflection or transmission coefficient as a function of frequency, i.e. the frequency response, from which the characteristics of the resonance can be derived as described on pp. 30-37 in [17]. The drive unit 41 or at least the receiving module will be coupled with the signal processing module 8 in order that the characteristics of the microwave field obtained is transferred to and can be processed in the signal processing module 8.

Figure 19:
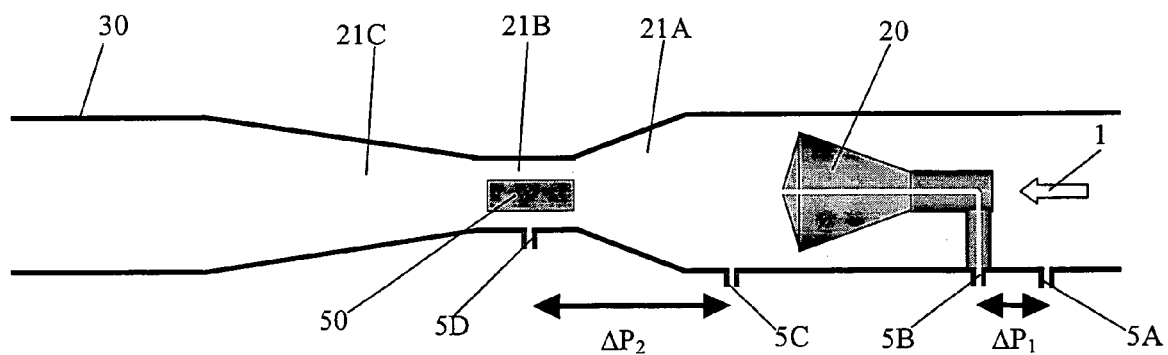
FIG. 19 shows an example of an embodiment of a 3-phase wet gas meter according to the invention using capacitance probes for dielectric measurements.

It is also, as an alternative to the microwave based water detection, possible to use a capacitance type of dielectric measurement to determine the water content, as exemplified in FIG. 19. Capacitance electrodes 50 are arranged in such a manner that the total capacitance is determined by the wet gas stream 1 flowing in the pipe 30. A capacitance measurement, such as e.g. described in the Reference [18], can then be combined with a double DP unit to make up a 3-phase wet gas meter. Typically the capacitance electrodes will be coupled to the signal processing module 8 via a drive electronics module, similarly to the microwave sensor illustrated in FIG. 20.

In summary, the invention disclosed herewith provides a 3-phase wet gas meter concept which is capable of measuring the individual flow rates of gas, liquid hydrocarbons and water in a wet gas stream. This is a new way of combining a double DP and a water detection unit (e.g. a microwave resonator).

This new device and method for 3-phase measurement concept yields a lowered uncertainty of the wet gas flow rate measurement as compared to a 2-phase gas/liquid concept because of the possibility to quantify the liquid (water+ liquid hydrocarbons) properties.

Further, 3-phase wet gas meter according to this invention can be made compact because the same sensor geometry can be used for the fluid composition measurement and for the flow rate measurement.

| Abbreviations: | |
|---|---|
| DP | Differential pressure |
| DDP | Double Differential pressure |
| GVF | Gas Volume Fraction |
| PVT | Pressure Volume Temperature |

| Symbols | |
|---|---|
| $A_{constriction}$ | Flow cross section in flow meter constriction - minimum cross section |
| $A_{pipe}$ | Flow cross section in flow meter pipe |
| $C_d$ | Flow meter discharge |
| D | Pipe inner diameter |
| $f_0$ | Resonant frequency in vacuum |
| $f_{mix}$ | Resonant frequency with fluid filled sensor |
| $f_{mw}$ | Microwave resonant frequency |
| $Q_g$ | Gas volumetric flow rate |
| $Q_{g0}$ | Gas volumetric flow rate - calculated assuming single phase gas flow rate |
| $Q_l$ | Liquid volumetric flow rate |
| $V_{A/B}$ | Volume of component A |
| $X_{LM}$ | Lochard Martinelli number |
| y | Fluid (wet gas) expansibility |
| $\alpha_A$ | Volume fraction of component A |
| $\alpha_c$ | Liquid hydrocarbons volume flow fraction |
| $\alpha_g$ | Gas volume flow fraction |
| $\alpha_l$ | Liquid volume flow fraction |
| $\alpha_w$ | Water volume flow fraction |
| $\alpha_{c0}$ | Initial guess liquid hydrocarbons volume flow fraction |
| $\alpha_{g0}$ | Initial guess gas volume flow fraction |
| $\alpha_{w0}$ | Initial guess water volume flow fraction |
| $\beta$ | Flow meter beta ratio |
| $\epsilon$ | Permittivity (dielectric constant) |
| $\epsilon_c$ | Permittivity of liquid hydrocarbons |
| $\epsilon_g$ | Permittivity of gas |
| $\epsilon_{hc}$ | Permittivity of hydrocarbon phase |
| $\epsilon_{mix}$ | Permittivity of fluid mixture |
| $\epsilon_w$ | Permittivity of water |
| $\Delta p$ | Differential pressure |
| $\Delta p_g$ | Differential pressure from single phase gas flow |
| $\Phi_g$ | 2-phase gas multiplier |
| $\rho_c$ | Liquid hydrocarbons density |
| $\rho_g$ | Gas density |
| $\rho_l$ | Liquid density |
| $\rho_w$ | Water density |

REFERENCES

[1] Nyfors, E., A. Wee, "Measurement of mixtures of oil, water, and gas with microwave sensors. New developments and field experience of the MFI MultiPhase, and WaterCut Meters of Roxar", *Proc. Subsurface Sensing Technologies and Applications II, at SPIE's 45th Annual Meeting*, San Diego, July-August 2000, pp. 12-21, Invited.

[2] Ø. Lund Bø, E. Nyfors, T. Løland, J. P. Couput, "New compact Wet Gas Meter based on a microwave water detection technique and differential pressure flow measurement" 20th North Sea Flow Measurement Workshop, 2002.

[3] E. Nyfors, Ø. Lund Bø, "Kompakt strømningsmåler", Norsk patent, 315584.

[4] E. Rhodes, "Device and method for determining flow rates in a two-phase stream", European patent EP0076882, 1981.

[5] T. V. Nguyen, "Methods for metering two-phase flow", U.S. Pat. No. 4,576,043, 1984.

[6] P. R. Daniel and J. S. Lund, "A meter for the measurement of multiphase fluids and wet gas", International patent WO0208702, 2002.

[7] J. R. Fincke, Improved method and system for measuring multiphase flow using multiple pressure differentials. WO patent WO122041, 2001.

[8] International standard ISO 5167-1: *Measurement of fluid flow by means of pressure differential devices.*

[9] D. Chisholm, "Two-phase flow in pipelines and heat exchangers", *Longman Inc*, 1983, Chap. 11.

[10] D. Chisholm, "Flow of Incompressible Two-Phase Mixtures throughsharp edged Orifices", *Journal of Mechanical Engineering Science*, Vol 9, No 1, 1967.

[11] D. Chisholm, "Research Note: Two-Phase flow through sharp edged Orifices", *Journal of Mechanical Engineering Science*, Vol 19, No 3, 1977.

[12] H. De Leeuw, "Liquid correction of Venturi meter Readings in Wet Gas Flow", North Sea Flow Measurement Workshop, 1997.

[13] F. McCall, Fluid flow meter, U.S. Pat. No. 4,638,672, 1987.

[14] A. Sihvola, Electromagnetic mixing formulas and applications, Inst. of Electrical Engineers, 1999, ISBN 0 85296 772 1, Ch. 9.

[15] Tiuri, M. E., E. G. Nyfors, P.-V. Vainikainen, S. H. Ståhl, *Mittausmenetelmä ja -laite kiinteän, rakeisen aineen massavirtauksen ja kosteuden tai jonkin muun ominaisuuden määräämiseksi. (Method and device for measuring the material flow and the moisture, or some other property, of a solid, granular material; in Finnish)*, Suomi-Finland patent No. 69372, filed 30.12.1983.

[16] Nyfors, E. G., Å. Bringsvor, Måler, særlig for kontinuerlig måling av blandingsforholdet mellom to fluider som strømmer i rør, f.eks. vanninnhold i olje; samt fremgangsmåte for gjennomføring av slik måling. (Meter, especially for the continuous measurement of the mixing ratio of two fluids flowing in a pipe; and method for performing such measurements; in Norwegian), Norwegian patent No. 308.922, Filed Jun. 3, 1988.

[17] Nyfors, E., *Cylindrical microwave resonator sensors for measuring materials under flow*, Thesis, Helsinki Univ. of Tech., Radio Lab. Report S243, May 2000, 181 p.

[18] E. Hammer, E. Dykesteen, "Fremgangsmåte og instrument for måling av trekomponents medium", Norsk patent, 304333.

The invention claimed is:

1. Flow meter capable of measuring the individual flow rates of gas, liquid hydrocarbons, and water in a predominantly gas-containing flowing fluid mixture comprising:

a water content meter comprising a microwave resonator for providing a signal representing a measure of the water content of said fluid mixture based on a measure of dielectric permittivity, a double differential pressure generating unit DDP-unit for measuring two differential pressures in said fluid and for providing therefrom two measurement signals representing two independent values of differential pressure in said fluid mixture, a signal processing unit having inputs capable of receiving said two measurement signals and said water content signal, and a calculation module for calculating values representing the volumetric flow rates of said gas, liquid hydrocarbons and water in said fluid mixture, and wherein said DDP-unit and said microwave resonator are combined in a common structure.

2. Flow meter according to claim 1, wherein the DDP-unit comprises two topologically different differential pressure (DP)-generating structures, installed close to each other in a pipe such that one DP-generating structure influences the flow pattern at the other DP-generating structure.

3. Flow meter according to claim 1, wherein the DDP-unit comprises a single flow cross section reduction device mounted in said fluid flow such as to vary cross section of said fluid flow, and two differential pressure measuring structures arranged to measure differential pressures at two different positions at or near said flow cross section reduction device.

4. Flow meter according to claim 3, wherein said flow cross section reduction device comprises an oblong body.

5. Flow meter according to claim 3, wherein the single flow cross section reduction device defines an inlet region, a reduced cross section region and an outlet region, the DDP-unit comprises a first differential pressure measuring device arranged in one of the said regions, and a second differential pressure measuring device is arranged in another one of said regions.

6. Flow meter according to claim 3, wherein both differential pressure measuring structures are arranged to measure accelerational pressure drops.

7. Flow meter according to claim 3, wherein one differential pressure measuring structure is arranged to measure accelerational pressure drop and the other differential pressure measuring structure is arranged to measure pressure recovery.

8. Flow meter according to claim 1, wherein the DDP-unit comprises a V-cone and a Venturi tube; wherein said V-cone is used in the microwave resonator.

9. Flow meter according to claim 1, comprising a body placed centrally in a pipe and an orifice, wherein said central body is used in the microwave resonator.

10. Flow meter according to claim 1, where the common structure is a single oblong body, said oblong body being used to both to generate two independent differential pressures and as part of a microwave resonator.

* * * * *